United States Patent [19]

Sorge et al.

[11] Patent Number: 5,663,062
[45] Date of Patent: Sep. 2, 1997

[54] OLIGONUCLEOTIDE LIBRARIES USEFUL FOR PRODUCING PRIMERS

[75] Inventors: Joseph A. Sorge, Rancho Santa Fe; Dan Shoemaker, Del Mar, both of Calif.

[73] Assignee: Stratagene, La Jolla, Calif.

[21] Appl. No.: 159,719

[22] Filed: Nov. 30, 1993

Related U.S. Application Data

[63] Continuation of Ser. No. 863,412, Apr. 3, 1992, abandoned.

[51] Int. Cl.$^6$ .................... C12P 19/34; C07H 21/04
[52] U.S. Cl. .................... 435/91.1; 536/24.3; 536/24.33; 536/25.3
[58] Field of Search .................... 435/6, 91.1, 810; 536/24.33, 24.3, 25.3

[56] References Cited

U.S. PATENT DOCUMENTS

| | | | |
|---|---|---|---|
| 4,321,365 | 3/1982 | Wu et al. | 536/27 |
| 5,028,534 | 7/1991 | Sadler et al. | 435/69.2 |
| 5,114,839 | 5/1992 | Blöcker | 435/6 |

FOREIGN PATENT DOCUMENTS

WO 89/11211  11/1989  Germany.

OTHER PUBLICATIONS

Landegren et al., "A Ligase–Mediated Gene Detection Technique," *Science*, 241:1077–1080 (1988).

Studier, "A Strategy for High–volume Sequencing of Cosmid DNAs: Random and Directed Priming with a Library of Oligonucleotides," *Proc. Natl. Acad. Sci. USA*, 86:6917–6921 (1989).

Szybalski, "Proposal for Sequencing DNA Using Ligation of Hexamers to Generate Sequential Elongation Primers (SPEL–6)," *Gene*, 90:177–178 (1990).

Bains, "Setting a Sequence to Sequence a Sequence," *Biotechnology*, 10:757–758 (1992).

Haymarie et al., *Nucleic Acids Res.* 14(21), 8615–8624 (1986).

Hofer et al., *Eur. J. Biochem.* 167, 307–313 (1987).

D'Souza et al., *Biochem. Cell. Biol.* 67, 205–209 (1989).

Khorana, *Science* 203, 614–625 (1979).

*Primary Examiner*—Kenneth R. Horlick
*Attorney, Agent, or Firm*—Pennie & Edmonds; Albert P. Halluin

[57] ABSTRACT

A library of oligonucleotides is described comprising a plurality of different oligonucleotides each in separate containers. The oligonucleotides are typically of the same length of from about 5 to 10 nucleotides in length, and each oligonucleotide in the library has the same nucleotide sequence of from 1 to 3 nucleotides in length at the 5' terminus of all the oligonucleotides in the library. In addition methods are described for using the oligonucleotide library for producing oligonucleotides of preselected nucleotide sequence for use in DNA sequencing and primer extension reactions.

34 Claims, 3 Drawing Sheets

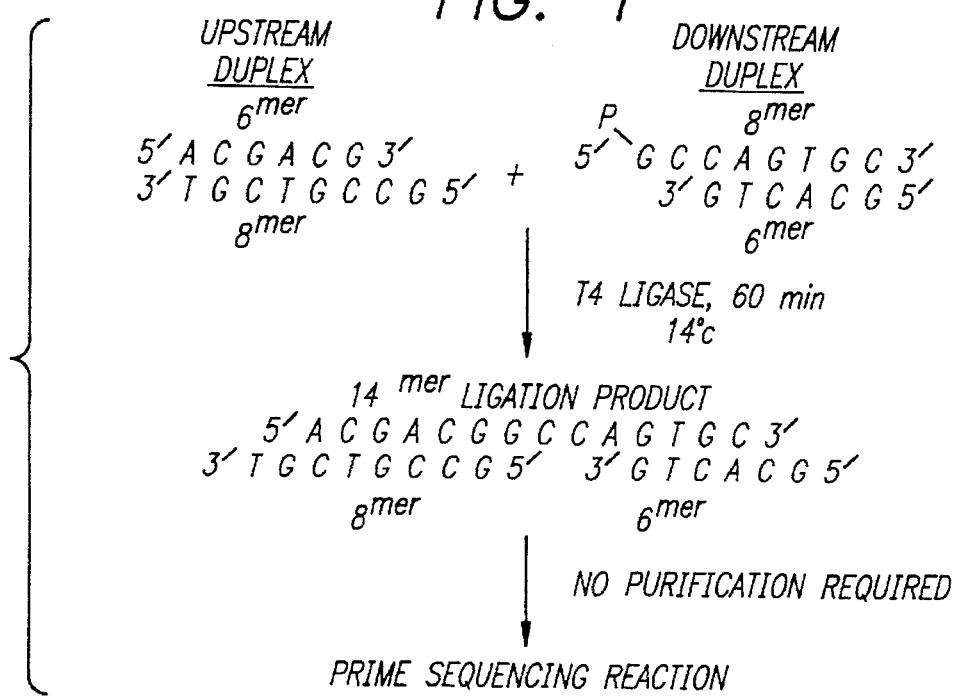
FIG. 1
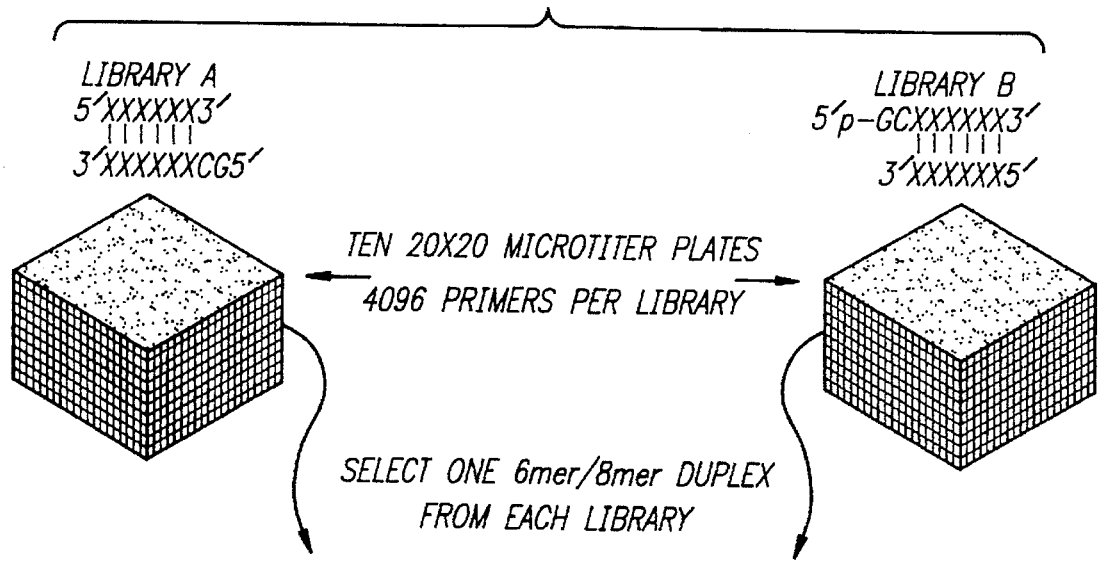
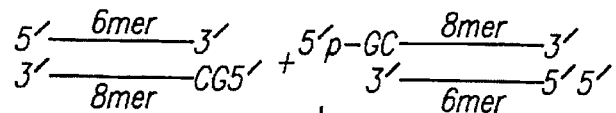
FIG. 2
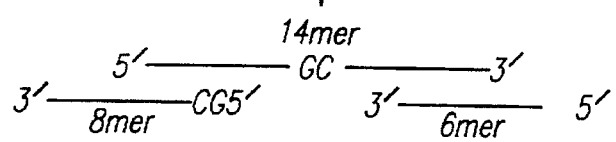

OLIGONUCLEOTIDE LIBRARIES USEFUL FOR PRODUCING PRIMERS

This is a continuation of application Ser. No. 07/863,412 filed on Apr. 3, 1992, abandoned.

DESCRIPTION

1. Technical Field

The present invention relates to libraries of oligonucleotides. In addition, the invention describes methods using the libraries of oligonucleotides to produce oligonucleotides of preselected nucleotide sequence.

2. Background

Oligonucleotides are widely utilized in molecular biological manipulations including DNA sequencing, cycle sequencing, polymerase chain reactions, in vitro mutagenesis, cloning methodologies involving polylinkers and adapters, synthesis of genes by hybridization and ligation of multiple oligonucleotides, and the like methods. Traditionally, oligonucleotides are prepared by chemical synthesis methods de novo each time they are required. Chemical synthesis of oligonucleotides is time consuming and costly.

One approach to DNA sequencing is called "primer walking" which utilizes known sequence information of a target nucleic acid to be sequenced to design a distal primer which is then used to obtain additional, downstream sequence information. Although primer walking is conceptually appealing, because of its simplicity and the ordered nature of the sequence information obtained, the method is expensive and time-consuming because after each sequence is determined, a new, customized primer must be chemically synthesized. Because a single oligonucleotide synthesis requires the preparation of more oligonucleotide than is required for the single sequencing step to be performed, material is wasted resulting is excess cost, and synthesis time slows the sequential sequencing steps.

Recently, Studier proposed a strategy to simplify the preparation of unique oligonucleotides in the form of a library of pre-synthesized oligonucleotides representing every possible nucleotide sequence in the size range of oligonucleotides from 8 to 10 nucleotides in length. Studier, *Proc.Natl.Acad.Sci.*, 86:6917–6921 (1989). However, the library poses technical difficulties insofar as the library must contain from $4^8$ (65,536) to $4^{10}$ (1,048,576) members, respectively, which is generally considered to be so large as to be unmanageable. In addition, oligonucleotides of 8 mer to 10 mer length are less preferred sequencing primers than longer oligonucleotides of 12 mer to 18 mer length.

Szybalski proposed the use of a library of hexameric oligonucleotides comprising every possible combination of nucleotide bases, representing a library having $4^6$ (4,096) members, as a means to reduce the size of the library. Szybalski, *Gene*, 90:177–178 (1990). Theoretically, pairs of hexamers from the library were proposed to be capable of being individually ligated while hybridized to a template to form 12 nucleotide (nt), 18-nt, or 24-nt oligonucleotides in length, thereby forming every possible nucleotide sequence from a library having 4,096 members. This approach requires ligation of the hexamer pairs in the presence of template DNA. A disadvantage is that the amount of produced oligonucleotide is limited by the quantity of target sites on the template DNA. In addition, it has been determined in our experiences that template-driven ligation is not reproducible depending on the sequence of the template. Secondary structures within the template are believed to contribute to the variability in natural template-driven ligation.

The possibility exists for using a hexamer oligonucleotide library according to Sybalzski et al, supra, to provide complementary oligonucleotides to form duplex DNA which could be joined in a blunt-end ligation reaction.

Blunt-end ligation of flush-ended DNA segments (duplex DNA fragments) has been described by Pfeiffer et al, (*Nucl.Acids Res.*, 11:7853–7871, 1983) using T4 DNA ligase in the presence of high concentrations of oligonucleotides. The use of blunt end ligation of duplex DNA fragments was attempted to solve the above described problems of unmanageable library size and variabilities in template-driven ligations. However, new difficulties were observed using blunt-end ligation, namely that the ligation was of low efficiency, and was difficult to control and prevent concatamerization or misoriented ligation products.

It has now been discovered that the above problems in joining blunt-ended duplex DNA fragments can be overcome by ligation of duplex DNA having cohesive termini.

BRIEF SUMMARY OF THE INVENTION

In accordance with these discoveries, the invention describes a library for producing oligonucleotides of preselected nucleotide sequence comprising from about 100 to 100,000 oligonucleotide members in the library, each of said members having: a) a length of at least 5 nucleotides, b) sequence complementarity along 5 contiguous nucleotides with at least one other member of the library, and c) a nucleotide sequence that upon complementary hybridization with another member forms a duplex DNA molecule with an overhang and a blunt end.

In a related embodiment, the invention describes a library for producing an oligonucleotide of preselected nucleotide sequence comprising a plurality of oligonucleotides, each having a different nucleotide sequence. The oligonucleotides in the library (library members) have the same length and are from 6 to 10 nucleotides in length. Additionally, the oligonucleotide members in the library all have a sequence according to the formula XN, where N is any nucleotide sequence from 5 to 10 nucleotides in length and X is any nucleotide sequence of at least one nucleotide in length that is common to all oligonucleotides in the library. Preferably, the individual oligonucleotide members of the library are each present in separate packages.

The invention also contemplates methods of using the libraries to form oligonucleotides of preselected sequence, and kits containing the libraries.

BRIEF DESCRIPTION OF THE DRAWINGS

FIG. 1 illustrates a typical ligation reaction according to the present methods using 6 mer/8 mer DNA duplexes as examples to form a 14 mer oligonucleotide primer (SEQ ID NO 1) of preselected sequence.

FIG. 2 is a flow chart diagramming the steps in a ligation method for producing a oligonucleotide having a preselected nucleotide sequence using two libraries (A and B) according to the methods described herein. The flow chart shows a preferred embodiment using 6 mer/8 mer duplex DNA molecules having cohesive GC termini, with the 8 mer oligonucleotide of library B having a phosphorylated 5' terminus to form a 14 mer.

Figure 4:
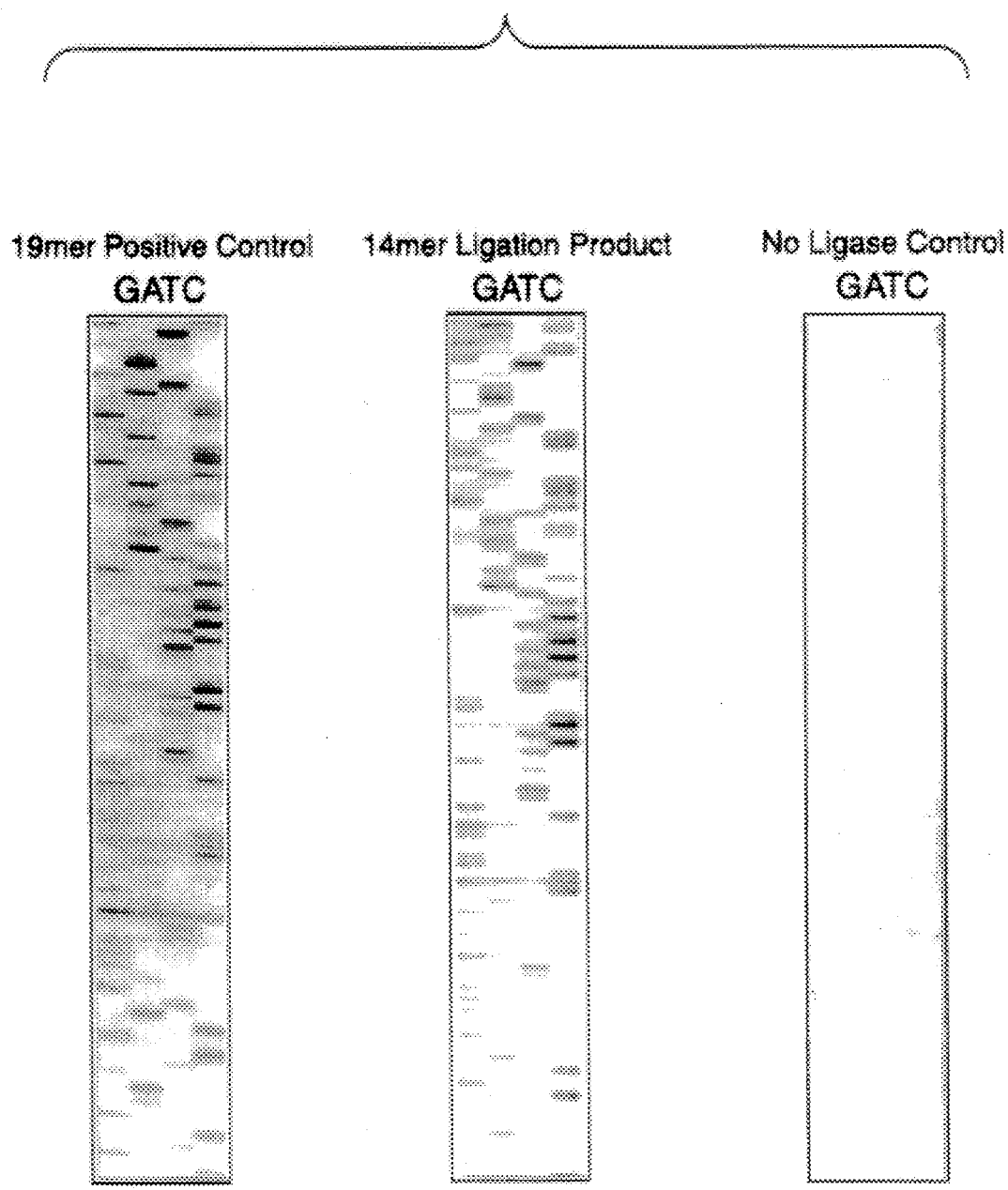

FIG. 4 illustrates the sequencing results of cycle-sequencing ssM13mp18 using an oligonucleotide 14 mer primer produced as described in Example 4. The left panel shows a sequencing gel profile produced using the 19 mer positive control (Primer A'), the center panel shows a sequencing gel profile produced using the 14 mer ligation product (primer A), and the right panel shows a sequencing gel profile produced using the ligation reaction product when no ligase is added to the ligation reaction.

DETAILED DESCRIPTION OF THE INVENTION

A. Definitions

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. The nucleotides are adenine, thymine, cytosine, guanine and uracil.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Oligonucleotide: The term "oligonucleotide" or "oligo" as used herein in reference to primers, probes and nucleic acid fragments or segments to be synthesized by ligation of oligonucleotides is defined as a molecule comprised of two or more deoxyribonucleotides or ribonucleotides, preferably at least 5. Its exact size will depend on many factors, which in turn depends on the ultimate conditions of use.

Gene: A nucleic acid whose nucleotide sequence codes for an RNA or polypeptide. A gene can be either RNA or DNA.

Complementary Bases: Nucleotides that normally pair up when DNA or RNA adopts a double stranded configuration.

Complementary Nucleotide Sequence: A sequence of nucleotides in a single-stranded (ss) region of DNA or RNA capable of hybridizing to another single-stranded region for a length of time sufficient to permit the desired reaction, e.g., a ligation reaction or a primer extension reaction.

Conserved: A nucleotide sequence is conserved with respect to a preselected (reference) sequence if it non-randomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine-like or pyrimidine-like nucleotide that differs structurally from A, T, G, C, or U, but is sufficiently similar to substitute for the normal nucleotide in a nucleic acid molecule.

Upstream: In the direction opposite to the direction of DNA transcription, and therefore going from 5' to 3' on the non-coding strand, or 3' to 5' on the coding strand or mRNA.

Downstream: Further along a DNA sequence in the direction of sequence transcription, that is traveling in a 3'- to 5'-direction along the non-coding strand of the DNA or a 5'- to 3'-direction along the coding strand.

B. Oligonucleotide Libraries

The present invention is directed at solving the problem of rapid and inexpensive synthesis of oligonucleotide primers for use in DNA sequencing, cycle sequencing and polymerase chain reaction (PCR) procedures. The approach described herein utilizes oligonucleotide libraries that are used to form oligonucleotides of preselected sequence suitable for use as primers in molecular biological manipulations, particularly for DNA sequencing and PCR.

The oligonucleotide library is a collection (plurality) of oligonucleotide members, each having a different preselected nucleotide sequence, that can be used to construct larger oligonucleotides of preselected sequence by combining the members. In order to build any possible nucleotide sequence by combining members, the library preferably contains every possible combination of nucleotide sequence.

The size of a library is determined by the expression $4^n$ where "n" represents the number of bases in each of the oligonucleotide subunits making up the library. Thus, a small increase in oligonucleotide length dramatically increases the size of the library. For example, a library of oligos having 6 nucleotide bases, also referred to as a 6 mer, contains 4096 different oligos, whereas a 9 mer library has over 260,000 primers.

In accordance with the present invention, two or more double-stranded (ds) DNA duplexes which have complementary overhanging (cohesive) termini are ligated to form a ligation product comprising a larger oligonucleotide of preselected sequence. The cohesive termini on the duplexes increase the specificity and reaction rate of the ligation reaction. The use of a DNA duplex comprised of a 6 mer and an 8 mer (a 6 mer/8 mer duplex) having a two nucleotide overhang is used as exemplary, and is shown in FIG. 1. The downstream duplex contains a phosphate group on the 5' terminus of its 8 mer to provide a ligation substrate for DNA ligase. Note that the ligation product is a 14 mer on the upper (sense) strand and two non-ligated oligonucleotides on the lower (non-coding) strand because of the absence of a 5'phosphate on the 5' end of the 8 mer in the upstream duplex.

All duplexes of this invention have two domains: an overhang formed by the longer oligonucleotide in the duplex, and a region of complementarity between the oligonucleotides of the duplex whose length is defined by the length of the shorter oligonucleotide in the duplex.

Extending the reaction scheme of FIG. 1, the present invention contemplates duplexes having at least one, and preferably 1 to 3, nucleotides in the complementary overhangs, although a two base overhang is preferred. Furthermore, the length of the oligonucleotide in the region of complementarity in a duplex is at least 5 nucleotides, and is preferably 5 to 10 nucleotides, although it is particularly preferred when the complementarity is formed by 5 to 6 nucleotides because of the resulting library size, as discussed further herein. Thus, the invention utilizes duplexes comprised of one the following pairs of oligonucleotide structures: duplexes having a one nucleotide overhang: 5 mer/6 mer, 6 mer/7 mer or 7 mer/8; having a two nucleotide overhang: 5 mer/7 mer, 6 mer/8 mer or 7 mer/9 mer; or having a three nucleotide overhang: 5 mer/8 mer, 6 mer/9 mer or 7 mer/10 mer. Particularly preferred are 5 mer/7 mer or 6 mer/8 mer duplexes.

In one embodiment, the invention contemplates the ligation of two duplexes having structures as described above and shown in FIG. 1.

Although the example shown in FIG. 1 illustrates a 5' overhang on both duplexes A and B, the invention can also be practiced with complementary 3' overhangs.

Alternatively, the oligonucleotides forming the oligonucleotide components of the upstream and downstream duplexes can be added together to form a ligation reaction admixture in the form of oligonucleotides rather than as duplexes. In this embodiment, and using the 6 mer/8 mer duplex as exemplary, two 6 mer oligonucleotides and two 8 mer oligonucleotides are added together to form a ligation reaction admixture. This embodiment is described in Example 2 herein. The admixed oligonucleotides first anneal to their respective complementary oligonucleotides to form the two (upstream and downstream) duplexes, such as is shown in the first step of FIG. 1, and subsequently are ligated by DNA ligase to form a ligation product as described herein.

Using either approach for producing an oligonucleotide of predetermined nucleotide sequence, the present invention contemplates providing one or more libraries of oligonucleotides designed to allow the user to select specific oligonucleotides from the library to build an oligonucleotide of preselected sequence.

Although exemplary and preferred, the invention is not to be limited to the ligation of two duplexes (A and B) having complementary overhangs as shown in FIG. 1. Also contemplated is the ligation of three or more duplexes, for example, duplexes A, B and C, each having overhangs adapted to direct the orderly assembly by hybridization and ligation of the three duplexes to form a ligated oligonucleotide. In this case, duplex B has a first and second overhang, duplex A comprises an overhang complementary to the first overhang of duplex B, and duplex C comprises an overhang complementary to the second overhang of duplex B. Furthermore, the overhang of C is not complementary to either first overhang of duplex B or to the overhang of duplex A, thereby preventing unwanted hybridizations and ligations. A similar rationale is applied to the ligation of 4 or more duplexes according to the present invention.

In each case, the methods can be practiced by providing oligonucleotides into a hybridization admixture, or by providing pre-assembled duplexes and admixing the duplexes. Preferably, the methods are practiced by selecting oligonucleotides or duplexes from a library of this invention.

Thus the present invention contemplates two distinct types of libraries: duplex DNA libraries and oligonucleotide libraries.

1. Double-Stranded (Duplex) DNA Libraries

A first class of libraries contains double-stranded (duplex) DNA molecules, referred to as duplex DNA or a duplex. For example, using a 6 mer/8 mer duplex as exemplary, a library would have up to 4096 different members representing all possible nucleotides sequences in the hexanucleotide (6 mer) component of the 6 mer/8 mer duplex. All members of the library have the same nucleotide sequence in the overhang. Typically, each different duplex is present in a separate enclosure.

In one preferred embodiment, the oligonucleotide of the duplex providing the overhang is adapted for ligation to the terminal 3' nucleotide of another oligonucleotide to direct ligation between two duplexes, designated upstream and downstream duplexes to connote that upon ligation, a single, ligated oligonucleotide of preselected sequence is formed. Such adaptation is preferably in the form of a 5'-terminal phosphate on one overhanging oligonucleotide and a 5'-terminal hydroxyl group on the other overhanging oligonucleotide to permit enzymatic ligation of only one strand and not its complementary oligonucleotide. Other reactive moieties that function as the adaptation means may also be applied to the present technology as to provide directed ligation, and are therefore contemplated.

Thus the library can be provided with or without a 5' phosphate on the oligonucleotide of the duplex that contributes to the overhang. For example, in one embodiment of a 6 mer/8 mer duplex library, the 5' terminus of all the 8 mers in the library contain a phosphate.

Phosphorylation of the 5' termini of oligonucleotides is well known in the art. A useful phosphorylating reaction admixture comprises 30 microliters (ul) of a reaction buffer containing 50 mM Tris-HCl, pH 7.5, 10 mM $MgCl_2$, 5 mM DTT, 0.1 to 10 micrograms (ug) of oligonucleotide, 1 mM ATP, 50 micrograms of bovine serum albumin and 20 units of bacteriophage T4 polynucleotide kinase. The phosphorylating admixture is then maintained (incubated) at 37° C. for 30 minutes, whereupon the reaction is stopped, typically by adding 1 μl of 0.5M EDTA to the maintained admixture. If desired, [gamma-$^{32}$P] ATP can be added to the reaction to produce labeled oligonucleotide.

In preferred embodiments, the invention contemplates matched first and second libraries, where the first library comprises 6 mer/8 mer duplexes lacking a 5'phosphate on the 8 mer, and the second library comprises 6 mer/8 mer duplexes each having a 5'phosphate. The libraries are "matched" because the overhang of the oligonucleotides in the first library are complementary to the overhang in the second library.

An exemplary and preferred embodiment of two matched libraries is shown in FIG. 2, wherein the first and second libraries (represented as libraries A and B) each comprise up to 4096 different duplex DNA members present in separate wells of a microtiter plate, each member comprised of a 6 mer/8 mer duplex and having complementary GC overhangs formed by the 8 mer component.

Thus one embodiment contemplates a library comprised of a plurality of members, each member comprising a different duplex. Each duplex member of the library is present in a separate enclosure (package). Each duplex member has a unique nucleotide sequence and each duplex in the library has the same nucleotide sequence in the overhang region of the duplex. The region of complementarity in the duplexes of the library is at least 5, and preferably from 5 to 7, nucleotides in length, thereby defining the size of the library. Preferably the region of complementarity, and therefore the length of the shorter oligonucleotide of the duplex is 6 nucleotides, and therefore the library has a size of 4096 oligonucleotide members. The overhang is at least one nucleotide, and preferably is 1 to 3 nucleotides in length.

A preferred library has a dinucleotide overhang where the overhangs have a sequence selected from the group consisting of GG, CC, TT, AA, TC, CT, GA, AG, TG, GT, AC, CA, GC, CG, TA, AT, XI and IX, where X is selected from the group consisting of A, T, G and C, and where I is inosine.

Because the primers produced by the present invention are to be utilized in primer extension reactions, the presence of a common region of sequence in the center of the primer derived from the overhang puts a limitation on the use of the primer. To find a complementary match in a template, one must scan a region of the template for the occurrence of the common sequence in order to design a primer to that region. For example, if the library used has a two base overhang, e.g., GC, then template must be scanned for the presence of the complementary CG in order to design a primer to hybridize to that region. The statistical likelihood of locating a CG in a random sequence is one in 16.

It is preferred to design the overhang in a manner to reduce the amount of template sequence that must be scanned in order to locate a match to the overhang region of the primer being produced by the present methods.

To that end libraries having the overhanging nucleotide sequence XI or IX are preferred, particularly CI or IC. By this design, both the first and second libraries can have the same termini, thereby reducing the number of different libraries required to represent every possible sequence. The presence of inosine (I) in the resulting oligonucleotide primer increases the probability of identifying a template sequence having a sequence complementary to the region of the primer derived from the overhang region, as discussed above.

In another embodiment, the invention contemplates the use of the dinucleotide TA or AT in the overhang region. Because thymidine is a small pyrimidine, a mismatch in the overhang region when the oligonucleotide is used as a primer can be tolerated. The internally mismatched nucleotide "T" in the primer will still allow the primer to effectively prime PCR and sequencing reactions. Thus, this approach also increases the probability of finding a sequence in a template to be primed that has complementarity to the primer oligonucleotide.

2. Oligonucleotide Libraries

In another embodiment, the invention contemplates a second class of library for producing oligonucleotides of preselected nucleotide sequence comprised of different oligonucleotides each present in a separate enclosure and each having a different nucleotide sequence.

The library, in one embodiment typically has at least 100 members, preferably about 100 to 100,000 different members, more preferably 1,000 to 10,000 members, and still more preferably about 4096 members. Each member of the library has a length of at least 5 nucleotides, preferably 5 to 10 nucleotides, although longer oligonucleotides can be present in the library. Each member has a sequence that is complementary with at least one other member of the library along a linear (contiguous) stretch of at least 5 nucleotides. Each member of the library has a nucleotide sequence such that it forms, upon complementary hybridization with another member of the library, a double-stranded (ds) duplex DNA molecule having a blunt end at one terminus and an overhang at the other terminus. The individual members of this library can vary in length and in sequence from one another, so long as the library is designed as defined above to allow the selection of hybridizable pairs to form duplex DNA having the overhangs as required to practice the methods of this invention.

In preferred embodiments, a library is comprised of a plurality of oligonucleotides each having a "common" (i.e., shared by all the members) nucleotide sequence of at least 1 nucleotide, and preferably from 1 to 3 nucleotides, in length located at one terminus of the oligonucleotide, which terminus is the same in each oligonucleotide member of the library.

The oligonucleotide members of a library in this embodiment can therefore be represented by the formula XN, where X represents the nucleotide sequence that is the same in all members of the library, and N represents the nucleotide sequence that is different for each member of the library. Preferably, N defines the region of complementarity when present in a duplex of the present invention. X is at least one nucleotide in length, preferably from 1 to 3 nucleotides in length, more preferably 2 nucleotides long, and N can be from 5 to 10 nucleotides in length, preferably 6.

In one embodiment, X defines the 5' terminus of the oligonucleotide. In another embodiment, all the members of the library have a 5' phosphate, preferably at the terminus of the oligonucleotide defined by X. In another embodiment, the invention contemplates a library where all the oligonucleotide members are free from phosphate.

Particularly preferred oligonucleotide libraries are comprised of oligonucleotides as described above but having a dinucleotide termini that has a sequence selected from the group consisting of GG, CC, TT, AA, TC, CT, GA, AG, TG, GT, AC, CA, GC, CG, TA, AT, XI and IX, where X is selected from the group consisting of A, T, G and C, and I is inosine. Preferably, the dinucleotide termini is CI, IC, TA or AT for the reasons described earlier.

3. Oligonucleotide Synthesis

The oligonucleotide compositions of the present invention can be prepared using any suitable method, such as, for example, the phosphotriester or phosphodiester methods see Narang et al., *Meth. Enzymol.*, 68:90, (1979); U.S. Pat. No. 4,356,270; and Brown et al., *Meth. Enzymol.*, 68:109, (1979). Exemplary synthesis is described in Example 1.

The oligonucleotides can be labeled, i.e., operatively linked to an indicating means or group, and used to detect the presence of a specific nucleotide sequence in a target template. Typically such indicating means is a label such as radioactive atoms, chemically modified nucleotide bases, and the like.

Radioactive elements operatively linked to or present as part of a oligonucleotide provide a useful means to facilitate the detection of a DNA duplex. A typical radioactive element is one that produces beta ray emissions. Elements that emit beta rays, such as $^3H$, $^{12}C$, $^{32}P$ and $^{35}S$ represent a class of beta ray emission-producing radioactive element labels. A radioactive oligonucleotide is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate forming compound such as an EDTA-analogue so that a fluorescent lanthanide complex is formed. See U.S. Pat. Nos. 4,374,120, 4,569,790 and published Patent Application Nos. EP0139675 and WO87/02708.

Biotin or acridine ester-labeled oligonucleotides and their use to label oligonucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligo, such as non-hybridized labeled oligo, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is 32P. Southern, *J. Mol. Biol.*, 98:503 (1975).

Nucleotide bases other than the common four nucleotides (A,T,G or C), or the RNA equivalent nucleotide uracil (U), can be used in the present invention and are designated nucleotide analogs. The property of a nucleotide analog is that it can be incorporated in a duplex DNA molecule without destabilizing the structure of the duplex. Thus a nucleotide analog can be a nucleoside with a non-destabilizing moiety, such as a non-protruding side group.

By non-destabilizing hybridization is meant that the nucleotide can participate in DNA-DNA or DNA-RNA duplex formation (base pairing) without significantly preventing the ordinary complementary hybridization of adjacent nucleotides in the oligonucleotide that would otherwise hybridize to their complement. Inosine is an example of a non-destabilizing hybridizable nucleotide, with specificity for A, T or C, but not G. Other nucleotides having this property can also be used in the present invention.

In addition, other modifications are contemplated that are designed to increase an oligonucleotide's resistance to degradation by exonucleolytic enzymes. A preferred modification is to have a thio-phosphodiester linkage between the terminal and penultimate nucleotide at the 3' terminus of an oligonucleotide used in a library or method of this invention.

C. Methods for Producing Oligonucleotides of Preselected Sequence

The invention contemplates methods for producing an oligonucleotide of preselected nucleotide sequence by combining the subunit oligonucleotides of a library described herein. The combining step generally involves ligation of two duplex DNA molecules having complementary cohesive (overhanging) termini, and having known nucleotide sequences. By selecting the duplex DNA molecules, or oligonucleotide subunits for assembling the duplexes, from a pre-made library, the method simplifies the process by eliminating the need for de novo chemical synthesis.

In one embodiment, the method generally comprises the steps of:

a) providing in an aqueous ligation buffer an admixture of first and second double-stranded (ds) DNA molecules of preselected nucleotide sequence, each of said ds DNA molecules comprised of two hybridized oligonucleotides that form an overhang, said oligonucleotides having a length of at least 5 nucleotide bases, and the overhangs comprised of at least one nucleotide base, wherein the sequence of said first ds DNA overhang is complementary to the sequence of said second ds DNA overhang, to form a ligation reaction admixture;

b) hybridizing the overhangs of said first and second ds DNA molecules to form a ligation reaction substrate; and c) ligating said ligation reaction substrate to form a ligation reaction product containing said oligonucleotide of preselected nucleotide sequence.

Preferably the oligonucleotide provided in step (a) is 5 to 10 bases in length and the overhangs are from 1 to 3 bases in length, and more preferably the overhangs are 2 bases long.

Typically, the provided ds DNA molecules are selected from a library of ds DNA molecules as described herein.

Insofar as hybridization occurs rapidly, the providing step and the hybridizing step can be performed simultaneously.

Ligation can be effected by any means that results in the formation of a phosphodiester bond between adjacent 3' hydroxyl and 5'phosphate groups of adjacent oligonucleotides. These ligations means can include chemical or enzymatic methods. Particularly preferred enzymatic means are conducted by the use of bacteriophage T4 DNA ligase, as exemplified herein.

In preferred embodiments, the overhang is a 5' overhang. In a particularly preferred embodiment, the 5' overhang of one duplex is phosphorylated.

In addition, rather than admixing duplex DNA molecules, the present method for producing an oligonucleotide of preselected nucleotide sequence can be practiced by providing oligonucleotides according to this invention having preselected nucleotide sequences as to form the above-defined duplexes having complementary termini.

Thus in one embodiment, first and second oligonucleotides are provided that can hybridize to form a first duplex DNA, and third and fourth oligonucleotides are provided that can hybridize to form a second duplex DNA. The sequence of the four provided oligonucleotides are preselected as to form the first and second duplex DNA molecules such that they have complementary overhangs.

In a related embodiment, oligonucleotides are selected from a library of this invention having sequences preselected to hybridize and form the desired ds DNA molecules. Thus, in this embodiment, the method comprises:

a) selecting at least one oligonucleotide from a library of this invention;

b) hybridizing in an aqueous ligation buffer the oligonucleotide(s) selected in step (a) having a preselected nucleotide sequence and capable of hybridizing to form a ligation reaction substrate; and c) ligating the ligation reaction substrate to form a ligation reaction product containing the oligonucleotide of preselected nucleotide sequence.

A ligation reaction substrate is a structure where the complementary overhangs of two (or more) ds DNA molecules are hybridized so as to provide a 3'-hydroxylated terminus immediately adjacent to a 5'-phosphorylated terminus. A ligation reaction product is a ligation reaction substrate having had a ligation reaction performed between the adjacent 3'-hydroxylated terminus and the 5'-phosphorylated terminus resulting in a phosphodiester bond between the 3' and 5' termini. An exemplary structure after ligation is shown in FIG. 1.

In one embodiment, a means for directing the hybridization of complementary overhangs is contemplated to selectively direct the hybridization of the desired overhangs. To that end, it is preferred to use combinations of nucleotide sequences in the two complementary overhangs that prevents self hybridization. This is accomplished by using sequences in the overhang which are not self-complementary. An example of self complementarity are the sequences AT, TA, GC and CG when present in an overhang.

In addition, hybridization direction can be affected by the kinetics of the reaction between complementary termini. For example, the use of molar excesses of one species, will favor hybridization between species rather than self hybridization of the minority species.

A preferred method comprises (1) selecting a first oligonucleotide from a first library defined by the formula XN as defined previously, (2) phosphorylating the selected oligonucleotide, (3) admixing the phosphorylated oligonucleotide with a second and third oligonucleotide selected from a second library defined by the formula N and a fourth oligonucleotide selected from the first library. The four oligonucleotides have preselected nucleotide sequences as to hybridize and form a ligation reaction substrate.

Alternatively, first, second and third libraries are provided: the first and second libraries having an oligonucleotide defined by the formula XN as before, where oligonucleotides from the second library contain 5' phosphorylated termini, and the third library having an oligonucleotide defined by the formula N. In this alternative, no phosphorylation step is required.

In another embodiment, the provided oligonucleotides having a 5' phosphate contains a thiol-phosphodiester linkage between the penultimate nucleotide and the 3' terminal nucleotide. The thiol linkage reduces the resulting ligated oligonucleotide's susceptibility to exonucleolytic degradation, increasing the lifetime of the oligonucleotide in primer extension reactions.

1. Hybridization of Oligonucleotides to Form a Ligation Reaction Substrate

A hybridization reaction mixture is typically prepared by admixing effective amounts of one or more oligonucleotide composition of the present invention, and other components compatible with a hybridization reaction. These oligonucleotide compositions can be two ds DNA molecules having complementary overhangs, three ds DNA molecules having complementary overhangs, or oligonucleotides having sequences that, upon hybridization, form the above ds DNA molecules.

The hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The phrase "hybridizing conditions" when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanidine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are typically carried out at temperatures from 4 degrees C. (4° C.) to 37° C., preferably about 12° C. to about 30° C., more preferably about 22° C., and for time periods from 0.5 seconds to 24 hours, preferably 2 minutes (min) to 1 hour. Exemplary are the conditions described in Example 2.

Effective amounts of the oligonucleotides to be ligated that are present in the hybridization reaction admixture are generally well known and are typically expressed in terms of molar ratios between the oligonucleotides or duplexes to be hybridized. Preferred ratios are hybridization reaction mixtures containing from equimolar to ten-fold excess amounts of the two species to be hybridized. As is well known, deviations from equal molarity will produce hybridization reaction products, although at lower efficiency. Thus although ratios where one of the two components (oligonucleotide A and oligonucleotide B or duplex A and duplex B as shown in FIG. 1) can be in as much as 100 fold molar excess relative to the other component, excesses of less than 50 fold, preferably less than 10 fold, and more preferably less the 2 fold are desirable in practicing the invention.

Effective concentrations of oligonucleotides in a hybridization reaction admixture are typically in the range of about 0.5 to 50 micromolar (uM), preferably about 1 to 10 uM, and more preferably about 5 uM.

In typical priming applications for an oligonucleotide of this invention, the template is double-stranded, and therefore both the sense and anti-sense strands can potentially serve as template for a primer. Duplicate priming in a single sequencing reaction is undesirable because it produces unreadable sequencing ladders, and could potentially occur if certain oligonucleotides of the duplexes to be ligated (that are complementary to the desired oligonucleotide primer) are available for priming reactions on the template strand opposite to the strand to be sequenced.

For example, according to the scheme of FIG. 2, three products are formed in the ligation reaction: a 14 mer, an 8 mer and a 6 mer. The 14 mer is the desired primer. The 8 mer could potentially act as a primer to the template strand complementary to the strand that the 14 mer will prime in low temperature primer extension reactions, thus providing the unwanted duplicate priming. The 6 mer could also theoretically prime, but is generally too short to initiate significant primer extension reactions. Thus it is desirable to block the capacity of the 8 mer in this example to prime.

In one embodiment, it is preferred that the sequence of the oligonucleotide that provides the overhang and that is complementary to the final ligated oligonucleotide primer (e.g., the 8 mer from duplex A in FIG. 2) has a 3' terminal nucleotide which is non-complementary to the sequence of its complementary oligonucleotide (e.g., the 6 mer from duplex A in FIG. 2). In this situation, the 8 mer from duplex A, which could otherwise provide a 3' terminus to initiate primer extension has a mismatch for the template to be extended at its 3' termini, and thus cannot prime the template. Thus, the mismatch prevents the 8 mer from participating in a priming event. The only 3' termini available that is able to prime a PCR or sequencing reaction is derived from the ligated oligonucleotide. The 8 mer from duplex A does not have a hybridizable 3' termini due to the mismatch design and is thereby inactivated.

With the design of a 3' mismatch as above, the ligation reaction product can be used directly in primer extension reactions without the need to purify the ligated oligonucleotide from the ligation reaction admixture.

Where the complementarity in the overhangs is selected to also be self-complementary, the use of unequal molar ratios can be utilized in one embodiment to favor hybridization and subsequent ligation of one pair over another. For example, referring to FIG. 2 that shows the hybridization of ds DNA molecules from library A and B, note that the sequence of the overhangs is self-complementary. To prevent self-ligation of the ds DNA molecules from library B, a ten fold excess of library A molecules will favor A-B combinations over B-B combinations. A-A combinations are prevented due to the absence of a 5'phosphate on the terminus of the ds DNA molecule. Thus, the combination of molar ratio imbalances and phosphorylation of only one of the two species allows an effective and reproducible method for producing oligonucleotides according to the present methods. This embodiment is described in the Examples.

2. Ligation of a Ligation Reaction Substrate to Form Oligonucleotide Primers of Preselected Sequence In producing a ligated oligonucleotide primer by the methods of this invention, the ligation reaction substrate is treated to ligation reaction conditions for a time period sufficient to form a phosphodiester bond between adjacent ligatable ends, namely between the 3' hydroxyl group at the 3'-terminus of oligonucleotide A and the 5' phosphate group at the 5'-terminus of oligonucleotide B. The product of an exemplary reaction is shown in FIG. 1.

The ligation step can be performed by any means available for forming a phosphodiester between the adjacent 5' and 3' termini, including enzymatic and chemical synthesis means. Preferred is the use of the enzyme ligase for catalytically inducing the ligation reaction.

Ligation reaction conditions are generally well known in the art and depend, in part, on the ligase to be used for forming the phosphodiester bond, and on the stability of the ligation reaction substrate.

A preferred ligase is bacteriophage T4 DNA ligase, such as is obtained from recombinant *Escherichia coli*, which can be obtained from a variety of commercial vendors.

Stability of the ligation reaction substrate is maintained by preserving hybridization reaction conditions during the manipulations after hybridization and during the ligation reaction. The substrate can vary in stability depending on the length of the hybridized oligonucleotide. For the shorter oligonucleotides contemplated by this invention, for example the hexameric oligonucleotides, it is preferred that hybridization and ligation reaction conditions be conducted below 30 degrees Centigrade (30° C.) and preferably between 4° C. and 22° C.

Ligation and hybridization can be accomplished in a single reaction step, and is preferred for convenience.

Ligation reaction conditions for ligation of the duplex DNA molecules typically require 0.5 to 50 uM duplex, preferably about 5 uM, or about 10 to 2000 nanograms (ng), and preferably about 50 to 1000 ng, of each oligonucleotide in a ligation reaction volume of 10 ul.

In one embodiment where the objective is to favor a preselected orientation of the ligated fragments rather than self-ligation, it is preferred to use about 5 to 10 fold molar excesses of the upstream (non-phosphorylated) duplex DNA molecule relative to the amount of the downstream duplex DNA molecule. Such a molar ratio reduces self-ligation of the downstream duplex DNA molecules. Other orientation-preference modifications can be utilized to further control the ligation reaction.

The ligation reaction conditions further require about 5 to 500 uM, preferably about 100 uM, rATP and 1× ligase buffer described herein. Preferably the ligation reaction admixture also contains about 0 to 25 percent, preferably 7 to 12, more preferably 10 percent by weight, polyethylene glycol (PEG) 8000 because the PEG increases the rate of the ligation reaction. Other ligase buffers can be utilized, as is well known. The important factors in the present ligation method are the concentrations of the rATP and the input oligonucleotides, as described herein.

Ligase used in the present method is preferably T4 DNA ligase at a concentration of about 0.5 to 10, preferably about 1 to 5 , Weiss units per 10 ul ligation reaction volume.

Hybridization and ligation reaction temperatures depend, as is known on the GC content of the oligonucleotide to be hybridized. For example, a hexanucleotide duplex comprised of all AT pairs require lower temperatures, typically below 22 degrees Centigrade (C.) and while a hexanucleotide of all GC pairs will hybridize and ligate up to about 37 degrees C. Thus the preferred range, depending on nucleotide content is about 4 to 30 degrees, preferably about 10 to 25 degrees, and more preferably 14 to 22 degrees C. Ligation reaction times can vary from about 0.5 min to 2 hours, although typically 5 min to 1 hour, and more preferably 5 to 15 minutes, are utilized.

Thereafter, the ligation reaction product formed is recovered, thereby producing the oligonucleotide of preselected nucleotide sequence. Typically, recovery comprises simply collecting the ligation reaction product and using it directly without further manipulations. Alternatively, the ligated oligonucleotide can be separated from the non-ligated precursor oligonucleotides, e.g., the 6 mer and 8 mer in the ligation product shown in FIG. 2. Separation techniques can include size separation or affinity isolation based on the presence of a terminal group such a biotin and the like and described further herein.

The resulting ligated oligonucleotide primer (ligation reaction product) formed by the action of the ligation reaction conditions on the ligation reaction substrate can be isolated from the template or can be used directly as described further herein.

In preferred embodiments, the use of terminus modifications are contemplated that will control the ligation reaction and prevent unwanted ligations. An exemplary and preferred terminus modification is to phosphorylate the 5' terminus of the oligonucleotide to be ligated, but not phosphorylate the 5' terminus of the oligonucleotide in the complementary strand that participates in the overhang hybridization. See FIG. 1 for this example. The strategy provides at least two advantages.

First, the ligation reaction in this preferred strategy includes a 5'phosphate, and therefore, only the strand of choice is ligated, and not the oligonucleotides in the complementary strand. The result is that the non-ligated oligonucleotides are short relative to the ligated oligonucleotide. The short non-ligated oligonucleotides are too short to prime a PCR reaction or prime a DNA sequencing reaction. Therefore, it is not required that the non-ligated oligonucleotides be removed from the desired ligated oligonucleotide product prior to its use in PCR or sequencing reactions.

Second, insofar as 5' phosphate is required for enzymatic ligation by T4 DNA ligase, non-phosphorylated 5' termini cannot participate in self-ligations to form improper concatamers. Using FIG. 1 as an example, the ds DNA molecule from library A cannot form A-A ligations because the A molecule is not phosphorylated. This feature is used to direct ligations The separation of the oligonucleotide primer product from the shorter non-ligated oligonucleotides can be accomplished by a variety of means following denaturation which destabilizes the hybridized duplexes. Exemplary separation methods include size fractionation of the oligonucleotides after denaturation of the ligation reaction product on gel sieve chromatography, on polyacrylamide gels and the like sizing methods.

Recovery of one strand from the duplex containing a ligation reaction product can be accomplished by a variety of means if desired, although selective recovery of the ligated oligonucleotide is not required for either PCR, sequencing or cycle-sequencing as shown in the Examples. Modification of either of the oligonucleotides before ligation to introduce a terminal group which affords selective retrieval of the desired oligonucleotide primer product is a preferred means for retrieval.

The biotin-avidin affinity system used for detection of non-isotopically labelled nucleotides is readily adapted to affinity based retrieval systems. In that system, biotin is introduced onto the 3' terminus of the downstream oligonucleotide or onto the 5' terminus of the upstream oligonucleotide which become incorporated into the ligated oligonucleotide product (e.g., the 3' terminus of the 8 mer in library B or the 5' terminus of the 6 mer in library A of FIG. 2). Thereafter, the presence of the biotin "tag" provides the means to selectively retrieve by elution the desired ligation reaction product.

The recovering step comprises the steps of admixing ligation reaction product having a biotin modified terminus with a suspension containing a solid phase comprising a solid support having avidin or streptavidin affixed thereto, to form an avidin binding admixture containing a liquid phase and a solid phase. Solid supports are generally well known, as are methods for fixing protein, such as avidin or streptavidin, to the solid support. Avidin or Streptavidin is available from a variety of commercial vendors.

The solid support can be in a variety of formats designed for easy recovery of the support away from the liquid phase to facilitate washing and eluting steps. These can take the form of beads, that can be physically separated based on size, by filtration or sedimentation. Alternatively, the solid support can have a functional property that makes separation simple, such as magnetism, or a biological binding affinity. Particularly preferred are magnetic beads that can be removed by magnetic fields.

The avidin binding admixture is then maintained under conditions compatible with a binding reaction between avidin and biotin for a time period sufficient for said avidin to bind to said biotin and form a biotin-avidin complex in the solid phase. The binding conditions are very flexible as the binding affinity between biotin and avidin is very high, and typically are aqueous solutions which do not denature DNA hybrids (duplex DNA). Time periods for binding are extremely fast, typically under one hour, and as fast as 1 to 10 minutes at room temperature.

The ligation reaction product is then eluted away from the solid phase to form the isolated oligonucleotide of preselected nucleotide sequence. Elution can be accomplished by any condition which disrupts (denatures) DNA duplexes to form single stranded oligonucleotides. Exemplary is the use of high temperature, e.g., greater than 65 degrees in 1× ligation buffer, or the like denaturing conditions, such as 0.1 to 0.5M NaOH.

3. Use in Directed Sequencing

Directed sequencing (primer walking) is a multi-step process in which a large sequence of nucleotides is determined by the steps of: (1) determining a first region of nucleotide sequence, (2) preparing a sequencing primer based on the downstream 3' region of the determined sequence to design the sequencing primer as to be complementary to the template at that downstream region, (3) determining a second region of nucleotide sequence using the sequencing primer designed from the previously determined sequence in a primer extension-based sequencing procedure (e.g., dideoxy sequencing), and (4) repeating steps (2) and (3) for as many cycles as needed to walk down the entire sequence to be determined. This approach is termed directed sequencing because the choice of primer directs the subsequent sequencing steps and thereby sequentially orders the sequence information obtained. Directed sequencing is typically compared to and preferred over random sequencing methods where the sequence information obtained is not directed in any particular order.

In preferred embodiments for practicing the present methods as applied to directed sequencing, the use of the oligonucleotide compositions provide a particular advantage over previous directed sequencing methods.

For example, using previous techniques, after a region of nucleic acid sequence was determined, a new sequencing primer would be required to complete the next "directed" sequencing step. That required primer must be chemically synthesized, which consumes time and the expense of custom oligonucleotide synthesis.

By the present invention, the required sequencing primer can be constructed from a pre-existing "library" of oligonucleotide or duplex DNA compositions according to this invention by:

(1) selecting a nucleotide sequence in the region of the template for designing a directed sequencing primer, (2) selecting four oligonucleotide compositions or two duplex DNA compositions from one or more libraries of the present invention, as needed, to produce an oligonucleotide having complementarity to the region of the template selected for directed sequencing, and (3) following the methods herein for admixing and ligating the selected compositions to form the oligonucleotide primers of preselected sequence. In the process of forming the ligated oligonucleotide primer, the resulting ligation reaction product is ready for sequencing without further manipulation. Exemplary is the ligation of duplex DNA molecules to form a 14 mer oligonucleotide and sequencing of ssM13mp18 described in Example 2 and shown in FIG. 4.

The methods for producing ligated primers can be applied to a variety of methods for manipulating and analyzing nucleic acid molecules, as will be apparent to one skilled in the art.

For example, a ligation reaction product can be used in primer extension reactions to produce primer extension reaction products. After producing the ligation reaction product, the resulting oligonucleotide is used in a primer extension reaction to form a primer extension reaction product containing the ligated primer. By providing excess amounts, relative to template, of the oligonucleotide to a hybridization reaction one can cycle through successive rounds comprising (1) hybridization of the oligonucleotide primer, (2) primer extension, and (3) denaturation to remove the primer extension product. By doing so the excess oligonucleotides will repeatedly hybridize to the template and extend to cyclically produce primer extension product. This process is referred to as cycle-extending because repeated primer extension product is formed by cycling through the above steps.

In cycle-extending, the denaturation step is typically a heat treatment manipulation to melt the duplex DNA. Such heat treatment necessitates that the polymerase used in the primer extension step be heat stable, or that additional polymerase be added to each primer extension reaction admixture at each cycle. The primer extension step in cycle-extending is preferably conducted with a heat stable polymerase as described herein for the polymerase chain reaction (PCR) methods.

In a related embodiment, chain terminators such as are used in dideoxy sequencing reaction can be used in the primer extension step of the above cycle-extending method. This allows the repeated production of sequencing reaction products in a cycle-sequencing method. By including the reagents normally used in a dideoxy sequencing reaction at the primer extension step, one can produce amounts of sequencing reaction product in excess of the amount normally provided after one dideoxy sequencing reaction, thereby increasing the sensitivity of the normal sequencing reaction. An exemplary cycle-sequencing procedure is described in Example 4.

4. Use in PCR Reactions

Polymerase chain reactions (PCR) utilize primer extension primers in a pairwise array as is well known. The PCR reaction, however, consumes mass quantities of the primers as each primer becomes incorporated in the primer extension product at each PCR cycle. Therefore, the present oligonucleotide libraries and methods are particularly well suited to solving the problem of PCR primer preparation insofar as the PCR primers can be synthesized by ligation as described herein from the pre-existing libraries of this invention rather than chemically synthesized de novo.

For example, to conduct a PCR reaction on a DNA sequence, one selects the desired PCR primer pair, and determines for each primer, the 3' primer and the 5' primer, which oligonucleotides of preselected sequence to produce, using the present methods. Thereafter, one admixes the prepared oligonucleotide compositions with a target for PCR amplification to form a PCR reaction admixture, ready for the PCR reaction.

Other permutations on PCR reaction methodologies will readily be apparent to one skilled in the art.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

The PCR reaction is performed by mixing the PCR primer pair, preferably a predetermined amount thereof, with the template nucleic acid having the sequence to be amplified, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing an amplified PCR reaction product.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 µM dATP; 200 µM dTTP; 200 µM dCTP; 200 µM dGTP; and 2.5 units *Thermus aquaticus* DNA polymerase I (U.S. Pat. No. 4,889,818) per 100 microliters of buffer. Other exemplary PCR reactions are described in Example 3.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nucleic Acid Research*, 17:711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

D. Oligonucleotide Libraries Kits

Many of the reagents described herein (e.g., nucleic acids such as the oligonucleotides and duplex DNA molecules in a library of this invention) have a number of forms, particularly variably protonated forms. As the skilled practitioner will understand, representation herein of one form of a compound or reagent is intended to include all forms thereof.

The reagents described herein can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of oligonucleotide compositions, restriction enzyme(s), DNA polymerase, DNA ligase, or a combination thereof. An aliquot of each component sufficient to perform at least one ligation reaction will be provided in each container.

Kits useful for producing a preselected primer for sequencing of a specific nucleic acid sequence or for conducting a PCR amplification reaction using a primer extension reaction methodology also typically include, in separate containers within the kit, dNTPs where N is adenine, thymine, guanine and cytosine, and other like agents for performing primer extension reactions.

The reagent species of any system described herein can be provided in solution, as a liquid dispersion or as a substantially dry powder, e.g., the oligonucleotides of duplex DNA molecules may be provided in lyophilized form.

In one embodiment, the present invention contemplates a kit for producing an oligonucleotide of preselected priming specificity, which kit comprises a plurality of separate packages (containers) within an enclosure, each package containing a different oligonucleotide or duplex DNA molecules according to this invention.

Kits having a plurality of such compositions are also referred to herein as libraries.

In one embodiment a preferred library contains up to 4096 separate containers, each containing a different 8 mer as defined herein, where each 8 mer in the library has the same dinucleotide sequence at its 5' terminus. In a related embodiment a library contains up to 4096 separate containers, each containing a different duplex DNA molecule comprised a 6 mer/8 mer oligos, where each 8 mer has the same dinucleotide sequence at its 5' terminus. Exemplary is the library shown in FIG. 4.

In another embodiment, a kit comprises two libraries, a first having a shorter oligonucleotide and a second having a longer oligonucleotide according to the formula XN as described before, where the shorter oligonucleotide is complementary to the sequence N. Exemplary is a kit having a first library of 6 mers, and a second library of 8 mers, as described herein. Optimally, the 8 mer library is phosphorylated at the 5' termini.

The oligonucleotides of the first and second libraries have sequences such that the complementary hybridization of a member of the first library with a member of the second library forms a double-stranded DNA molecule having at least a one nucleotide base overhang of the second library oligonucleotide sequence, and such that the terminal nucleotide(s) of all oligonucleotides in the second library that form the overhang have the same nucleotide sequence. Preferably, the overhang formed by complementary hybridization is a 5' terminal overhang, and more preferably the overhang is a dinucleotide sequence selected from the group consisting of GG, CC, TT, AA, TC, CT, GA, AG, TG, GT, AC, CA, GC, CG, TA, AT, XI and IX, wherein X is selected from the group consisting of A, T, G and C, and wherein I is inosine.

Alternatively, a kit comprises three libraries, namely a 6 mer, an 8 mer, and an 8 mer that is phosphorylated at their 5' termini. This kit provides all the materials to assemble a pair of duplexes A and B without the need for the manipulative step of phosphorylation.

Preferred kits contain organized enclosures such that the different oligonucleotides are distributed in a preselected array. For example, a 96-well microtiter tray is an enclosure that provides an array of 96 containers (wells). A larger library can be comprised of a series of microtiter trays, such as is shown in FIG. 2. Such organized arrays provides a convenient and manageable way to identify and access the different members of the library, and is amenable to automated processes for oligonucleotide synthesis according to the present methods.

EXAMPLES

The following examples are intended to illustrate, but not limit, the present invention.

1. Oligonucleotide Synthesis

The oligonucleotides in these Examples were synthesized on an Applied Biosystems Inc. (ABI) DNA synthesizer, model 391 or 392, with ABI reagents at a 0.2 um scale using standard cyanoethyl phosphoramidite chemistry and deprotection protocols according to the manufacturer's instructions.

The oligonucleotides were chemically phosphorylated where appropriate at their 5'-end by the addition, and subsequent deprotection of, 1-Dimethoxytrityl-2, 2'-sulfonyldiethanol-1-CED™ phosphoramidite (ABI).

The crude oligonucleotides were purified by PAGE and then desalted and lyophilized by standard procedures.

The oligonucleotides used in these Examples are described in Table 1:

TABLE 1

| Oligo No.[c] | N-mer | Sequence |
| --- | --- | --- |
| 1 | 6 | 5'-ACGACG-3' |
| 2 | 8 | 5'-GCCGTCGT-3' |
| 3 | 8 | 5'-P-GCCAGTGC-3'[a] |
| 4 | 6 | 5'-GCACTG-3' |
| 5 | 14 | 5'-ACGACGGCCAGTGC-3'[b] |
| A' | 19 | 5'-TAAAACGACGACGGCCAGT-3' |
| B | 22 | 5'-TGATTCCAACGAGGAAAGCACG-3' |

[a]Oligonucleotide No. 3 is shown with a phosphate group at its 5' terminus.
[b]The sequence of oligonucleotide No. 5 shows the product of ligation of oligonucleotide Nos. 1 and 3, and is aligned over oligonucleotide A' to illustrate the common sequences.
[c]Oligo Nos. 5, A' and B are repectively SEQ ID NOS 1, 2, and 3.

2. Ligation of Oligonucleotides to Form a Ligation Reaction Product

The oligonucleotides Nos. 1, 2, 3 and 4 shown in Table 1 were synthesized, and oligonucleotide No. 3 was chemically phosphorylated on its 5' terminus, as described in Example 1. The oligonucleotides Nos. 1, 2, 3 and 4 so produced were admixed into a ligation reaction admixture containing the following in 1× ligation buffer (50 mM Tris-HCl, pH 7.5, 7 mM $MgCl_2$, 1 mM DTT): 10% PEG 8000, 100 uM rATP, 5 uM of each of oligonucleotides Nos. 1, 2, 3 and 4, and 4 units of T4 DNA ligase. The ligation reaction admixture was then maintained (incubated) at 14° C. for 60 minutes to allow the oligonucleotides to anneal to their complements to form duplexes, for the cohesive overhangs to hybridize, and for the ligation reaction to occur and form a ligation reaction product comprising a 14 mer hybridized to oligonucleotide Nos. 2 and 4. The reaction is shown in FIG. 1.

When analyzed on a 20% denaturing acrylamide gel, greater than 90% ligation efficiency was observed in the presence of ligase, whereas only nonligated oligonucleotides were observed in the absence of ligase. Similar ligation reactions conducted at 14° C. were greater than 90% complete after 5 minutes, and greater that 99% complete after 15 minutes.

In an alternate procedure, oligonucleotide No. 3 was phosphorylated by the use of T4 DNA kinase.

3. Ligation Reaction Product as a Polymerase Reaction Primer

The 14 mer oligonucleotide ligation reaction product produced in Example 2 was used directly, without purification from the ligation reaction admixture, as a polymerase chain reaction (PCR) primer. To that end, a PCR admixture was prepared by admixing the following in 1× PCR buffer (10 mM Tris-HCl, pH 8.3, 50 mM KCl 4 mM $MgCl_2$, 0.1% gelatin) 250 uM dATP, 250 uM dGTP, 250 uM dTTP, 250 uM dCTP, 5 ng ssM13mp18 template DNA, 200 ng of oligonucleotide No. B (22 mer), either 200 ng of oligonucleotide No. A' (19 mer) or 300 ng of ligation reaction product (14 mer) produced in Example 2, and 1 unit Taq DNA polymerase.

The PCR admixture was then cycled in a 9600 Gene Amplification System PCR thermocycler (Perkin Elmer Cetus) under the following conditions: first, the admixture was maintained at 95° C. for 5 minutes, next the admixture was cycled through the following three temperatures at the indicated times for 25 cycles: 95° C. for 5 seconds, 50° C. for 5 seconds, and 72° C. for 5 seconds; thereafter, the admixture was maintained at 72° C. for 5 minutes to form a PCR product.

Figure 3:
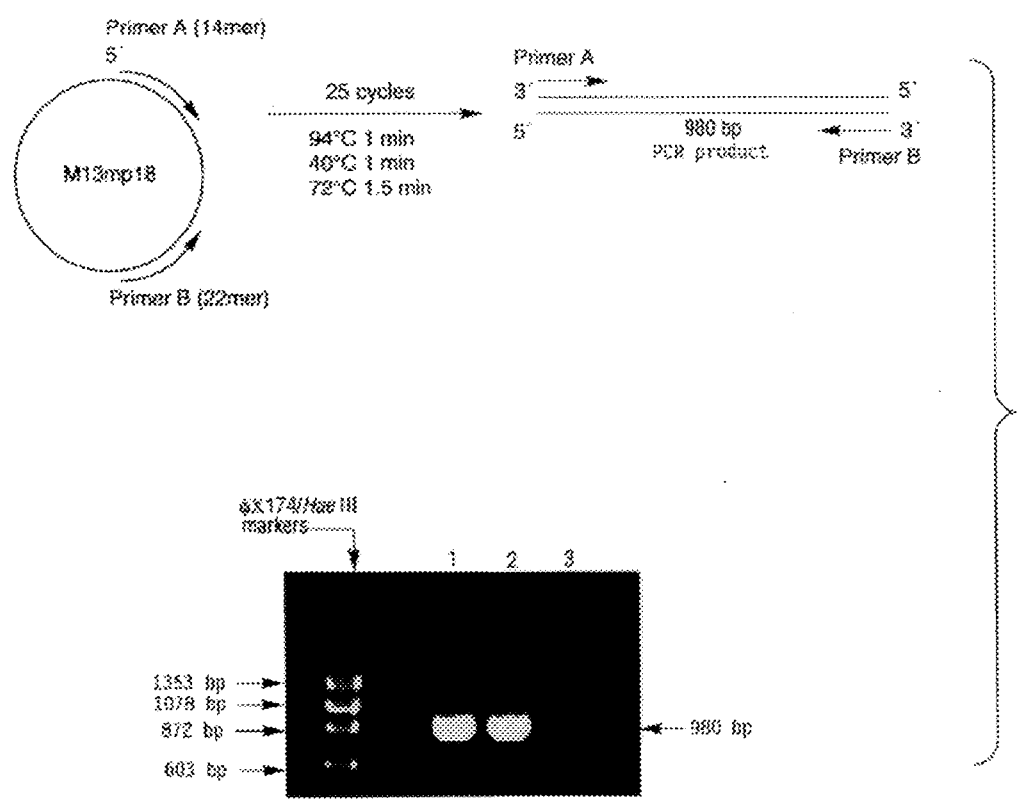
FIG. 3 illustrates an agarose gel electrophoretic analysis of the polymerase chain reaction (PCR) product formed using an oligonucleotide primer (14 mer) produced according to the ligation reaction shown in FIG. 1 as described in Example 3. The schematic in the upper portion of FIG. 3 illustrates the amplification by PCR of a 980 base pair (bp) fragment from an M13mp18 using a primer pair (primers A and B). The lower portion of FIG. 3 illustrates the agarose gel analysis showing that the 980 bp product was amplified from ssM13mp18 using the following primer pairs: Lane 1, 19 mer primer A' and 22 mer primer B; Lane 2, 14 mer primer A and 22 mer primer B; Lane 3, 6 mer/8 mer (no ligase control) and 22 mer primer B. Also shown is a lane of PhiX174/Hae II markers containing 1353, 1078, 872 and 603 bp fragments. The primer sequences are shown in Table 1 at page 43.

The resulting PCR product was analyzed by gel electrophoresis on a 1% agarose gel, the electrophoresed gel was stained with ethidium bromide, and the electrophoresed PCR products were visualized using ultraviolet light. The PCR reaction scheme and the gel analysis results are shown in FIG. 3.

Based on the template (ssM13mp18) sequence and the choice of PCR primers, a 980 base pair (bp) fragment is expected to be amplified by the use of either of the primer pairs B/A or B/A', where A is the 14 mer ligation reaction product formed in Example 2, and A' is the control 19 mer. An amplified 980 bp PCR product is observed when either the control 19 mer/22 mer (lane 1) or ligation reaction product 14 mer/22 mer (lane 2) primer pairs were used, indicating that a ligation reaction product formed by the present methods is able to prime template accurately in a PCR reaction when added to the PCR admixture as unpurified ligation reaction product. No PCR product is formed when ligase is not added to the ligation reaction admixture (lane 3) indicating that 6 mers and 8 mers are not able to prime in a PCR reaction under the conditions tested.

4. Cycle-Sequencing Using a Ligation Reaction Product as Primer

The 14 mer oligonucleotide in the ligation reaction product formed in Example 2 was used to prime a DNA sequencing reaction, in a cycle-sequencing format. To that end, a sequencing reaction admixture was prepared by admixing the following in 1× sequence buffer (10 mM Tris-KCl, pH 8.3, 50 mM KCl 4 mM $MgCl_2$, 0.1% gelatin): 0.5 uM dATP, 240 uM ddATP, 5 uM dGTP, 200 uM ddGTP, 5 uM dTTP, 200 uM ddTTP, 5 uM dCTP, 120 uM ddCTP, 10 uCi $\alpha^{33}$P-dATP (1332 Ci/mmole; 10 uCi/ml; New England Nuclear), 100 ng ssM13mp18 template DNA, either 10 ng of oligonucleotide No. A' (19 mer) or 10 ng of ligation reaction product (14 mer) produced in Example 2, and 1 unit Taq DNA polymerase.

The sequencing reaction admixture was then cycled in a 9600 Gene Amplification System PCR thermocycler (Perkin Elmer Cetus) under the following conditions: first, the admixture was maintained at 95° C. for 5 minutes, next the admixture was cycled through the following three temperatures at the indicated times for 30 cycles: 95° C. for 10 seconds, 50° C. for 20 seconds, and 72° C. for 30 seconds; thereafter, the admixture was maintained at 72° C. for 5 minutes to form a cycle-sequencing reaction product. The sequencing reaction was stopped by the addition of 5 uL of stop dye mix (90% formamide, 0.05% bromophenol blue, 0.05% xylene cyanol), and 2 ul was electrophoresed on a 6% acrylamide/7M urea sequencing gel.

The results of the sequencing gel analysis is shown in FIG. 4. The 14 mer ligation reaction product in unpurified form specifically primed a unique sequence ladder using the ssM13mp18 template, as shown in the center panel of FIG. 4. The sequence ladder produced by a chemically synthesized 19 mer (oligonucleotide A') primer was indistinguishable (left panel of FIG. 4) from the ladder formed by the ligation reaction product, indicating that primer produced by the present methods efficiently primes sequencing reactions. In the absence of ligase, no sequence ladder is seen (right panel) indicating that 6 mers and 8 mers do not significantly prime a sequencing reaction under the conditions utilized.

The foregoing specification, including the specific embodiments and examples, is illustrative of the present invention and is not intended to limit the invention in any way. It will be apparent to those skilled in the art that numerous variations and modifications to the above-described embodiments of the invention will be possible without departing from the spirit and scope of the invention. It is intended that the following claims be interpreted to embrace all such variations and modifications.

What is claimed is:

1. A library for producing an oligonucleotide of preselected nucleotide sequence comprising a plurality of oligonucleotide members having different nucleotide sequences, each of said oligonucleotide members having the same length and being from 6 to 10 nucleotides in length, said oligonucleotide members all having a sequence according to the formula XN, where N is any nucleotide sequence from 5 to 9 nucleotides in length and X is any nucleotide sequence of at least one nucleotide in length that is common to all oligonucleotide members in the library.

2. The library of claim 1 wherein N is 6 nucleotides in length.

3. The library of claim 1 wherein X is 2 nucleotides in length.

4. The library of claim 1 wherein N is 6 nucleotides in length, X is 2 nucleotides in length, and said library contains 4096 different oligonucleotide members.

5. The library of claim 1 wherein the sequence of X is selected from the group consisting of GG, CC, TT, AA, TC, CT, GA, AG, TG, GT, AC, CA, GC, CG, TA, AT, XI and IX, wherein X is selected from the group consisting of A, T, G and C, and wherein I is inosine.

6. The library of claim 1 wherein each oligonucleotide member has a 5' terminal phosphate.

7. The library of claim 1 wherein said X defines the 5' terminus of the oligonucleotide member.

8. A library for producing an oligonucleotide of preselected nucleotide sequence which library comprises a plurality of members, each member comprising a different double-stranded (ds) DNA molecule comprised of first and second hybridized oligonucleotides and having an overhang of at least one nucleotide, said first oligonucleotide having from 5 to 9 nucleotide bases, said second oligonucleotide having from 6 to 10 nucleotide bases, each of said overhangs on said different ds DNA molecules having the same nucleotide sequence.

9. The library of claim 8 wherein said overhang is from one to three nucleotide bases.

10. The library of claim 8 wherein said first and second hybridized oligonucleotides are a hexamer and one of a septanucleotide, octanucleotide or nonanucleotide.

11. The library of claim 8 wherein said first and second hybridized oligonucleotides are a heptanucleotide and one of a hexanucleotide, septanucleotide or octanucleotide.

12. The library of claim 8 wherein said first and second hybridized oligonucleotides are a hexanucleotide and an octanucleotide.

13. The library of claim 8 wherein said overhang is a dinucleotide selected from the group consisting of GG, CC, TT, AA, TC, CT, GA, AG, TG, GT, AC, CA, GC, CG, TA, AT, XI and IX, wherein X is selected from the group consisting of A, T, G and C, and wherein I is inosine.

14. The library of claim 8 wherein each oligonucleotide has a 5' terminal phosphate.

15. A kit containing one or more libraries according to claim 1.

16. A kit for producing an oligonucleotide of preselected nucleotide sequence, which kit comprises first and second libraries, each library comprising a plurality of members, each member comprising a different oligonucleotide, said first library comprising hepta-, hexa- or septanucleotides, said second library comprising septa, octa- or nonanucleotides, said oligonucleotides having a sequence such that the complementary hybridization of a member of said first library with a member of said second library forms a double-stranded DNA molecule having at least a one nucleotide base overhang of said second library oligonucleotide sequence, and such that the terminal nucleotide(s) of all oligonucleotides in said second library that form said overhang have the same nucleotide sequence.

17. The kit of claim 16 wherein said overhangs are 5' terminal.

18. The kit of claim 17 wherein said second library oligonucleotides have a 5'-terminal phosphate.

19. The kit of claim 16 wherein said first library comprises hexanucleotides and said second library comprises octanucleotides.

20. The kit of claim 16 wherein said overhangs have a sequence selected from the group consisting of GG, CC, TT, AA, TC, CT, GA, AG, TG, GT, AC, CA, GC, CG, TA, AT, XI and IX, wherein X is selected from the group consisting of A, T, G and C, and wherein I is inosine.

21. The kit of claim 19 wherein said first and second libraries each have 4096 different oligonucleotides.

22. The kit of claim 16 wherein said second library oligonucleotides have a thio-phosphodiester linkage between the penultimate nucleotide and the 3' terminal nucleotide.

23. A method for producing an oligonucleotide of preselected nucleotide sequence comprising the steps of:

a) selecting at least one oligonucleotide member from a library according to claim 1 or 8;

b) hybridizing in an aqueous ligation buffer the oligonucleotide member(s) selected in step (a) having a preselected nucleotide sequence and capable of hybridizing to form a ligation reaction substrate; and c) ligating said ligation reaction substrate to form a ligation reaction product containing said oligonucleotide of preselected nucleotide sequence.

24. A method for producing an oligonucleotide of preselected nucleotide sequence comprising the steps of:

a) selecting first, second, third and fourth oligonucleotides of preselected nucleotide sequence from a library according to claim 1, said first and second oligonucleotides having sequences such that their complementary hybridization forms a first double-stranded (ds) DNA molecule, said third and fourth oligonucleotides having sequences such that their complementary hybridization forms a second ds DNA molecule, and said first and second ds DNA molecules having complementary overhangs of at least one nucleotide base;

b) hybridizing in an aqueous ligation buffer an admixture of said first, second, third and fourth oligonucleotides, such that said complementary overhangs hybridize to form a ligation reaction substrate; and c) ligating said ligation reaction substrate to form a ligation reaction product containing said oligonucleotide of preselected nucleotide sequence.

25. The method of claim 24 wherein said overhangs are comprised of from one to three nucleotide bases.

26. The method of claim 24 wherein said overhangs are comprised of two nucleotide bases.

27. The method of claim 26 wherein said two base overhang on said first ds DNA molecule has a nucleotide sequence selected from the group consisting of GG, CC, TT, AA, TC, CT, GA, AG, TG, GT, AC, CA, GC, CG, TA, AT, XI and IX, wherein X is selected from the group consisting of A, T, G and C, and wherein I is inosine.

28. The method of claim 24 wherein said first or second ds DNA molecule is comprised of two hybridized oligonucleotides that are a hexanucleotide and one of a septanucleotide, octanucleotide or nonanucleotide.

29. The method of claim 24 wherein said first or second ds DNA molecule is comprised of two hybridized oligonucleotides that are a heptanucleotide and one of a hexanucleotide, septanucleotide or octanucleotide.

30. The method of claim 24 wherein said first or second ds DNA molecule is comprised of two hybridized oligonucleotides that are a hexanucleotide and an octanucleotide, and said overhangs have a nucleotide sequence selected from the group consisting of GG, CC, TT, AA, TC, CT, GA, AG, TG, GT, AC, CA, GC, CG, TA, AT, XI and IX, wherein X is selected from the group consisting of A, T, G and C, and wherein I is inosine.

31. The method of claim 30 wherein said overhangs have the sequence GC, CG, TA, AT, CI or IC.

32. The method of claim 24 wherein each of said ds DNA molecules has a 5' overhang and said second ds DNA molecule has a 5' terminal phosphate on said 5' overhang.

33. The method of claim 32 wherein the oligonucleotide in said second ds DNA molecule having a 5'-terminal phosphate contains a thio-phosphodiester linkage between the penultimate nucleotide and the 3' terminal nucleotide.

34. A method for producing an oligonucleotide of preselected nucleotide sequence comprising the steps of:

a) selecting first and second double-stranded (ds) DNA molecules of preselected nucleotide sequence from a library according to claim 8, each of said ds DNA molecules having complementary overhangs;

b) hybridizing in an aqueous ligation buffer an admixture of said first and second ds DNA molecules, such that said complementary overhangs hybridize to form a ligation reaction substrate; and b) ligating said ligation reaction substrate to form a ligation reaction product containing said oligonucleotide of preselected nucleotide sequence.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

ACGACGGCCA GTGC                                                                                          14

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TAAAACGACG ACGGCCAGT                                                                                     19

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TGATTCCAAC GAGGAAAGCA CG                                                                                 22